(12) United States Patent
Ina et al.

(10) Patent No.: US 8,173,588 B2
(45) Date of Patent: *May 8, 2012

(54) IMINOCARBOXYLIC ACID SALT-CONTAINING SOLID COMPOSITION AND PRODUCTION METHOD THEREOF

(75) Inventors: Tomomi Ina, Osaka (JP); Yasutaka Sumida, Osaka (JP)

(73) Assignee: Nippon Shokubai Co., Ltd., Osaka (JP)

(*) Notice: Subject to any disclaimer, the term of this patent is extended or adjusted under 35 U.S.C. 154(b) by 164 days.

This patent is subject to a terminal disclaimer.

(21) Appl. No.: 11/492,900

(22) Filed: Jul. 26, 2006

(65) Prior Publication Data

US 2007/0027206 A1    Feb. 1, 2007

(30) Foreign Application Priority Data

Jul. 27, 2005  (JP) ................. 2005-217887

(51) Int. Cl.
*A61K 31/195* (2006.01)
(52) U.S. Cl. ........................ 510/361; 510/276
(58) Field of Classification Search .............. None
See application file for complete search history.

(56) References Cited

U.S. PATENT DOCUMENTS

| | | | |
|---|---|---|---|
| 5,104,568 A * | 4/1992 | Shaw et al. ............... | 510/361 |
| 5,318,726 A | 6/1994 | Rossmaier et al. | |
| 5,958,866 A | 9/1999 | Donoghue et al. | |
| 6,063,302 A | 5/2000 | Asakawa et al. | |

FOREIGN PATENT DOCUMENTS

| | | |
|---|---|---|
| CN | 1434855 | 8/2003 |
| EP | 0 708 078 A1 | 4/1996 |
| EP | 0 892 040 A2 | 1/1999 |
| EP | 1 238 052 B1 | 9/2002 |
| JP | 09-104897 | 4/1997 |
| JP | 09-104897 A | 4/1997 |
| JP | 09-110813 | 4/1997 |
| JP | 09-110813 A | 4/1997 |
| JP | 2644977 B2 | 5/1997 |
| WO | WO-92/02489 A1 | 2/1992 |
| WO | WO-00/12463 A1 | 3/2000 |
| WO | WO-0144428 | 6/2001 |
| WO | WO-01/92449 A1 | 12/2001 |
| WO | WO-02/19981 A2 | 3/2002 |
| WO | WO-2005/116158 A1 | 12/2005 |

OTHER PUBLICATIONS

Office Action issued in related Japanese Application No. 2005-217887 on Jun. 7, 2011.

* cited by examiner

*Primary Examiner* — Walter Webb
(74) *Attorney, Agent, or Firm* — Connolly Bove Lodge & Hutz LLP

(57) ABSTRACT

Provided is a solid composition comprising an iminocarboxylic acid salt, wherein the iminocarboxylic acid salt is 3-hydroxy-2,2'-iminodisuccinic acid and/or a salt thereof. The solid composition comprises 70% by weight or more of the iminocarboxylic acid salt, relative to a solid content except for moisture of the solid composition, and the solid composition comprises 20% by weight or less of moisture, relative to the solid composition. Also a production method of the solid composition, comprising a step of drying an iminocarboxylic acid salt-containing composition is provided.

10 Claims, No Drawings

IMINOCARBOXYLIC ACID SALT-CONTAINING SOLID COMPOSITION AND PRODUCTION METHOD THEREOF

This application claims priority from Japanese Application 2005-217887 filed Jul. 27, 2005.

TECHNICAL FIELD

The present invention relates to an iminocarboxylic acid salt-containing solid composition and a production method thereof. More specifically, the present invention relates to: a chelate compound-containing composition useful in organic chelating agents, scale inhibitors, water treatment agents, detergent builders, bleaching assistants, masking agents, fiber treatment agents, additives for papers and pulps, cleaning agents for semiconductors, photographic chemicals, and soil modifiers; an iminocarboxylic acid salt-containing solid composition useful in various cleanings in various fields such as food industry, chemical industry, and machine industry, or useful in cleanings with automatic dish washers for household or institutional use; and a production method of such a solid composition.

BACKGROUND ART

Chelate compound-containing compositions can form a complex with various metal ions and the like. Therefore, such compositions have been preferably used in various applications such as organic chelating agents, scale inhibitors, water treatment agents, detergent builders, bleaching assistants, masking agents, fiber treatment agents, additives for papers and pulps, cleaning agents for semiconductors, photographic chemicals, and soil modifiers. Such compositions have been desired to be in solid states for convenience of transportation and storage.

With respect to a conventional chelate compound-containing composition, disclosed is an aqueous solution composition containing an iminocarboxylic acid having a specific structure, in which the isomer ratio (D-form/L-form (molar ratio)) of the aspartic acid skeleton of the iminocarboxylic acid salt is 1/0 to 0.7/0.3 or 0/1 to 0.3/0.7, and the content of the iminocarboxylic acid salt is 40 to 70% by weight (for example, referring to Japanese Patent No. 2644977, on pages 1 and 2). For such an aqueous solution composition, there is no description that the iminocarboxylic acid salt is made into solid states.

With respect to the iminodisuccinic acid compound sin-solid states, disclosed are: a powdery builder composition containing an iminodisuccinic acid compound and an inorganic metal salt, the composition being free from stickiness and having easy handle ability (for example, referring to Japanese Kokai Publication No. Hei-09-104897, on page 2); a powder containing animinodisuccinic acid compound and having a moisture absorption rate of 20% by weight/day or less under a constant air temperature of 23° C. and a constant moisture of 65%, the powder may being granulated; and a powder containing an iminodisuccinic acid compound and an inorganic metal salt and having a moisture absorption rate of 20% by weight/day or less under a constant air temperature of 23° C. and a constant moisture of 65%, and the powder may being granulated (for example, Japanese Kokai Publication No. Hei-09-110813). However, there are no suggestions and disclosures about the solubility of these powders, and there was a room for contrivance how to prepare powders excellent in solubility. These powders are produced by adding acid, an inorganic metal salt such as zeolites, a surfactant, or the like for adjusting the pH. However, compositions free from such additives and capable of being preferably used in various applications have been desired.

SUMMARY OF THE INVENTION

The present invention has been made in view of the above-mentioned state of the art. The present invention has an object to provide a solid composition as follows: having advantages for transportation and storage; having excellent solubility; exhibiting functions such as excellent detergency; and capable of being preferably used in various applications, and a production method of such a solid composition.

The present inventors have made various investigations about chelate compound-containing compositions. They have noted that an iminocarboxylic acid salt, especially 3-hydroxy-2,2'-iminodisuccinic acid (referred to as "HIDS acid" or simply "HIDS") and/or a salt thereof ("HIDS salt")(hereinafter, 3-hydroxy-2,2'-iminodisuccinic acid and the salt thereof together are referred to as "HIDS acid salt") have excellent detergency and biodegradability. HIDS or HIDS acid means that 4 carboxylic acid groups of one HIDS molecule have all acid form, that is, HIDS-4H. HIDS salt means that at least one of the 4 carboxylic acid groups of one HIDS molecule has a salt-form, for example, HIDS-1Na. They have found that if such iminocarboxylic acid salt is a solid composition having a moisture content of a specific amount or less, such a solid composition can exhibit excellent stability: for example, having low moisture absorption rate; exhibiting excellent handling ability; and hardly causing blocking, and therefore such a composition can have excellent solubility as well as advantages for transportation and storage. Further, they have found that if an isomer ratio of an iminocarboxylic acid salt is specified, the solid composition can be more excellent in solubility in water. They also have found that if the content of the iminocarboxylic acid salt is specified, the solid composition can be preferably used in various applications such as organic chelating agents, scale inhibitors, water treatment agents, detergent builders, bleaching assistants, masking agents, fiber treatment agents, additives for papers and pulps, cleaning agents for semiconductors, photographic chemicals, and soil modifiers. The solid composition is free from additives such as an acid, an inorganic metal salt such as zeolites, or a surfactant, and therefore can be preferably used in applications in which inclusion of such additives is not preferable. Thereby, the above-mentioned problems can be admirably solved. They have also found that a production method or a storage method of the iminodisuccinic acid solid composition free from additives, the composition being preferably used in various applications and exhibiting the above-mentioned functional effects can have advantages. Thereby, the present invention has been completed.

That is, the present invention is a solid composition comprising an iminocarboxylic acid salt, wherein the iminocarboxylic acid salt is 3-hydroxy-2,2'-iminodisuccinic acid and/or a salt thereof, the solid composition comprises 70% by weight or more of the iminocarboxylic acid salt, relative to a solid content except for moisture of the solid composition, and the solid composition comprises 20% by weight or less of moisture, relative to the solid composition. The solid content except for moisture of the solid composition is simply referred to as "solid content". The present invention is also a production method of the solid composition, comprising a step of drying an iminocarboxylic acid salt-containing composition.

The present invention is also a storage method of the solid composition, wherein the solid composition, is stored under an atmosphere of 42% relative humidity at 25° C.

DETAILED DESCRIPTION OF THE INVENTION

The present invention is described in more detail below.

The solid composition of the present invention is a solid composition comprising an iminocarboxylic acid salt, wherein the iminocarboxylic acid salt is 3-hydroxy-2,2'-iminodisuccinic acid and/or a salt thereof. The content of the above-mentioned iminocarboxylic acid salt (iminocarboxylate salt) is 70% by weight or more, relative to 100% by weight of the solid content. If the content of the iminocarboxylic acid salt is less than 70% by weight, the solid composition may insufficiently exhibit functions, and for example, may exhibit insufficiently improved detergency if used as a detergency. The above-mentioned content is preferably 70% by weight or more and 100% by weight or less. The lower limit of the content is more preferably 75% by weight or more, and still more preferably 80% by weight or more. The upper limit of the content is more preferably 98% by weight or less, and still more preferably 95% by weight or less.

The above-mentioned solid composition comprises 20% by weight or less of moisture, relative to 100% by weight of the solid composition. The solid composition may insufficiently exhibit excellent solubility if comprising more than 20% by weight of moisture, and the solid composition may have increased stickiness, thereby being difficult to handle if stored for a long period. The moisture content is more preferably 18% by weight or less, and still more preferably 15% by weight or less. The above-mentioned "comprising 20% by weight or less of moisture" means that the solid composition comprises more than 0 of moisture.

The above-mentioned solubility of the solid composition can be calculated from the following formula, at 5° C.:

Dissolution rate=(charged powder composition (mg))/(time taken for dissolution (sec))

The dissolution rate is preferably 0.6 mg/sec or more, and more preferably 1.8 mg/sec. or more, and still more preferably 2.0 mg/sec or more. The solid composition can be industrially sufficiently useful if showing a solubility within such a range.

The above-mentioned solid composition comprises 70% by weight or more and 100% by weight or less of an iminocarboxylic acid salt, relative to 100% by weight of the solid content, and also comprises 20% by weight or less of moisture, relative to 100% by weight of the solid composition. Therefore, the solid composition contains another component other than the iminocarboxylic acid salt if comprising 100% by weight or less of the iminocarboxylic acid salt, relative to the solid content.

The above-mentioned another component is not especially limited as long as the functional effects of the present invention can be exhibited. Examples of another composition include aliphatic polycarboxylic acids or salts thereof, amino acids or salts thereof, amino polycarboxylic acids or salts thereof, organic builders, inorganic builders, inorganic salts, dispersants, antifoaming agents, granulating agents, extenders, bleaching agents, bleaching activators, surface modifiers, anticorrosives, anti-redeposition agents, fluorescence agents, fungicides, enzymes, perfumes, and coloring agents. The solid composition may contain one or two or more species of them.

The content of the above-mentioned another component is calculated by deducting the content of the iminocarboxylic acid salt from 100% by weight of the solid content. If an inorganic salt is used as one component constituting the solid content, the content of the inorganic salt is preferably 5% by weight or less, relative to 100% by weight of the solid content.

The above-mentioned solid composition is useful inorganic chelating agents, scale inhibitors, water treatment agents, detergent builders, bleaching assistants, masking agents, fiber treatment agents, additives for papers and pulps, cleaning agents for semiconductors, photographic chemicals, and soil modifiers. Such a solid composition can be used in various applications, for example: various cleanings in various fields such as food industry, chemical industry, and machine industry; and cleanings with automatic dish washers for household or business use.

The solid composition of the present invention may be in any forms as long as it is in a solid state and comprises 70% by weight or more of the iminocarboxylic acid salt relative to the solid content, and 20% by weight or less of moisture relative to the solid composition. The solid composition may be in grain, powder, or granular form, for example.

The above-mentioned solid composition preferably has a particle diameter of 0.1 μm to 10 mm. The upper limit thereof is preferably 100 μm, more preferably 50 μm, and still more preferably 40 μm.

The iminocarboxylic acid salt is a compound represented by the following formula (1):

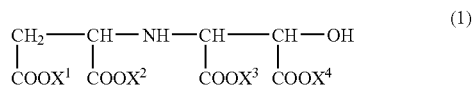

(in the formula, $X^1$ to $X^4$ may be the same or different and each represents a hydrogen atom, an alkali metal atom, or an ammonium group.)

In the above-mentioned $X^1$ to $X^4$, preferred examples of the alkali metal atom include lithium, sodium, potassium, rubidium, and cesium. Preferred examples of the alkali earth metal atom include magnesium, calcium, strontium, and barium. Preferred examples of the organic ammonium group (organic amine group) include alkylamine groups such as monoethylamine group, diethylamine group, and triethylamine group; alkanolamine groups such as monoethanolamine group, diethanolamine group, and triethanolamine group; polyamine groups such as ethylenediamine group and triethylenediamine group. Among them, each of the above-mentioned $X^1$ to $X^4$ is preferably sodium or potassium. The above-mentioned iminocarboxylic acid salt may be partially or completely neutralized.

Mentioned may be a method comprising reacting a starting material containing aspartic acid and/or salts thereof and epoxysuccinic acid in an aqueous medium, as the production method of the above-mentioned iminocarboxylic acid salt.

In the above-mentioned production method, the ratio of aspartic acid/and salts thereof to epoxysuccinic acid in the starting material as well as other reaction conditions such as reaction temperature are not especially limited. Both isomers, i.e. cis-isomer and trans-isomer may be used as the epoxysuccinic acid. The cis-isomer is more preferably used. The aqueous medium is water or a mixture of water and a solvent soluble in water. Preferred are water; and mixed solvents of water and methanol, ethanol, isopropyl alcohol, acetone or acetonitrile. Among these, water is preferably used.

The above-mentioned iminocarboxylic acid salt has a structure represented by the above formula (1), and therefore an optical isomer in which the aspartic acid skeleton may be in L-form or D-form is present.

The aspartic acid skeleton of the iminocarboxylic acid salt means a structure represented by the following formula (2) in the above-mentioned formula (1):

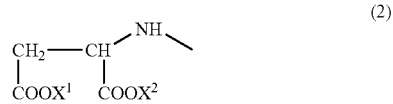

(2)

(in the formula, $X^1$ and $X^2$ may be the same or different and are the same as in the above-mentioned formula (1)).

The L-form and D-form of the aspartic acid skeleton as used herein mean the compounds whose configuration about the asymmetric carbon in the structure represented by the above formula (2) are S-configured and R-configured; thus the S-configured compound is the L-form and the R-configured compound is the D-form.

In the production method of the above-mentioned iminocarboxylic acid salt, the aspartic acid and/or salts thereof having a configuration of L-form or D-form are/is used as the starting material. Thereby, the aspartic acid skeleton of the iminocarboxylic acid salt correspondingly has a configuration of L-form or D-form. For example, if the D-form of aspartic acid and/or salts thereof are/is used as the starting material, the aspartic acid skeleton of the iminocarboxylic acid salt generated by reaction with epoxysuccinic acid is derived from the configuration of the starting material and therefore retained as D-form. Thereby, an iminocarboxylic acid salt in which the asymmetric carbon atom of the aspartic acid skeleton is in R-configuration is produced. The L- or D-iminocarboxylic acid salt can be produced by resolving a racemic iminocarboxylic acid salt.

In the above-mentioned iminocarboxylic acid salt, it is preferable that the isomer ratio of the aspartic acid skeleton, that is, the molar ratio of D-form/L-form (D-form/L-form=) is preferably 0/1 to 0.3/0.7, or 1/0 to 0.7/0.3. If the molar ratio of D-form/L-form is within the above-mentioned range, the solid composition can be excellent insolubility in water. The isomer ratio (molar ratio of D-form/L-form) is more preferably 0/1 to 0.2/0.8, or 1/0 to 0.8/0.2, and still more preferably 0/1 to 0.1/0.9, or 1/0 to 0.9/0.1. Examples of methods of adjusting the isomer ratio of the aspartic acid skeleton of the iminocarboxylic acid salt within the specified range, in the above-mentioned production method of the iminocarboxylic acid salt, include a method in which the reaction is carried out using a starting material containing aspartic acid and/or salts thereof whose D/L ratio is within the specified range, and a method which comprises synthesizing the D-form of iminocarboxylic acid salt and L-form of iminocarboxylic acid salt independently and blending them in the specified ratio.

The biodegradability of the above-mentioned imino carboxylic acid salt varies among the isomers. The D-form, racemic form, and L-form in this order show higher biodegradability. The racemic form is preferably used as an iminocarboxylic acid salt to be used in view of the biodegradability. More preferably, an iminocarboxylic acid salt in which the ratio of the L-form is higher is used.

The present invention is also a production method of the solid composition, comprising a step of drying an imino carboxylic acid salt-containing composition.

As the above-mentioned iminocarboxylic acid salt-containing composition, preferred are a solution containing the iminocarboxylic acid salt produced by the above-mentioned production method and the like, and an iminocarboxylic acid salt-containing composition in a solid state in which the content of the iminocarboxylic acid salt is less than 70% by weight or the moisture content is more than 20% by weight. Among them, an aqueous solution containing the iminocarboxylic acid salt is preferable in view of handling ability.

The above-mentioned aqueous solution of the iminocarboxylic acid salt preferably has a concentration of 10% by weight or more. The concentration is more preferably 20 to 60% by weight, and still more preferably 30 to 55% by weight. If the concentration is less than 10% by weight, energy needed for removal and drying of the solvent increases and time taken for removal and drying the solvent becomes longer, which is economically inefficient. In contrast, the concentration more than 60% by weight is not preferable because the aqueous solution has an increased viscosity and therefore becomes difficult to handle.

The concentration of the above-mentioned aqueous solution can be adjusted by condensation and the like. The aqueous solution of the iminocarboxylic acid salt is crystallized and obtained crystals are dissolved in water again to produce an aqueous solution having a suitable concentration. In this case, a hydrophilic organic solvent such as methanol and acetone is added into the aqueous solution of the iminocarboxylic acid salt to crystallize the iminocarboxylic acid salt. However, it is preferable that the concentration is adjusted by a method using no organic solvents in view of removal or disposal of the organic solvents.

The above-mentioned iminocarboxylic acid salt-containing composition is subjected to a drying step. The drying step is a step of drying the iminocarboxylic acid salt-containing composition, thereby adjusting the content of the iminocarboxylic acid salt and the moisture content within preferable ranges, respectively. Through such a step, the iminocarboxylic acid salt-containing solid composition of the present invention can be produced.

If the above-mentioned iminocarboxylic acid salt-containing composition is an aqueous solution of the iminocarboxylic acid salt, it is preferable that the aqueous solution is adjusted to a suitable concentration as mentioned above, and then subjected to the drying step.

In the above-mentioned drying step, used may be, for example, spray drying equipments such as spray dryer, drum dryers such as suction drum dryer and CD dryer, air flow dryers, fluidized dryers, rotary dryers with heating tube, thin film type evaporating concentration and powdering equipments, vertical agitating granulators such as Lodige mixer and kneader, box dryers, through-flow tray dryers, tunnel dryers, continuous through-flow dryers, rotary dryers, ditch type agitating granulators, vacuum box dryers, freeze dryers, cylindrical agitating vacuum dryers, infrared dryers, and microwave dryers. Among them, preferred are spray drying equipments such as spray dryer, drum dryers such as suction drum dryer and CD dryer, air flow dryers, fluidized dryers, rotary dryers with heating tube, thin film type evaporating concentration and powdering equipments, vertical agitating granulators such as Lodige mixer and kneader. As mentioned above, the most preferable embodiment of the present invention includes a production method of the solid composition, comprising a drying step using a spray drying equipment such as spray dryer.

The solid composition produced through the drying in the above-mentioned drying step may be further pulverized with suitable grinder equipment if needed, and may be further granulated. The solid compositions produced through the drying with a CD dryer, a spray dryer and the like, generally have a small bulk density and various particle diameters.

However, such solid compositions are subjected to the pulverizing and granulating treatments to have a bulk density and particle diameter within suitable ranges respectively, depending on applications. If the solid composition is used in granular detergent compositions as a builder, for example, the solid composition after the above-mentioned drying may be difficult to uniformly mix with detergent composition components. However, such a solid composition can have a bulk density of about 0.5 to 1 g/cc, which is a bulk density of a general compact detergent, by being subjected to the pulverizing and granulating treatment.

The above-mentioned granulating treatment is not especially limited as long as the solid composition of the present invention can have a suitable bulk density and a particle diameter. General granulators may be used. Among them, agitating granulators may be preferably used. Examples of the agitating granulators include horizontal agitating granulators such as high speed mixer produced by Fukae Powtec Corp., and vertical agitating granulators such as Loedige mixer produced by Loedige Corp. Among them, preferred are vertical agitating granulators capable of applying share in the gravity direction and easily increasing the bulk density. After granulated, the solid composition is further dried, if necessary, thereby becoming a solid composition in which the content of the iminocarboxylic acid salt is 70% by weight or more relative to the solid content, and the moisture content is 20% by weight or less relative to the solid composition.

The present invention is also a storage method of the solid composition, wherein the solid composition is stored under an atmosphere of 42% relative humidity at 25° C. Use of such a storage method makes it possible to maintain high quality such as excellent solubility and high detergency for a long period without hygroscopic.

In the above-mentioned storage method, the "atmosphere" means: an operating atmosphere for drying the powders (the solid composition) or charging them into a container for storage or transportation; and an atmosphere inside a container in which the powders are stored.

The above-mentioned relative humidity at 25° C. is 42% or less, and preferable 40% or less.

In the above-mentioned storage method of the solid composition, as long as the relative humidity is within the above-mentioned range, other conditions are not especially limited. The storage container maintains the quality of the solid composition. The material and shape of the storage container are not especially limited if the atmosphere outside the storage container during the storage becomes an atmosphere of a relative humidity of 42% or less at 25° C. However, if the atmosphere outside the storage container may vary, the storage container preferably can keep the relative humidity inside the container during the storage in the same state as at the start of the storage (that is, a material through which no moisture passes and which causes no increase in humidity inside the container even if the humidity outside the container increases, and a shape capable to seal). Specific examples of the material of the container include craft paper, polyethylene, vinyl, polypropylene, aluminum, and polylaminate. Among them, more preferable are polyethylene, polypropylene, aluminum, and polylaminate because such materials can keep the relative humidity constant.

With respect to the shape of the storage container, preferable is a container that can be sealed. And a bag-shaped container and a container with lid are preferable. Among them, a bag-shaped container is preferably because of excellent handling such as easy sealing. The lower limit of the thickness of the storage container is preferably 0.005 mm in view of strength of the container, sealing ability and the like. The lower limit thereof is more preferably 0.01 mm, and still more preferably 0.02 mm. The upper limit thereof is preferably 0.5 mm in view of handling ability. The upper limit thereof is more preferably 0.3 mm, and still more preferably 0.1 mm. The thickness of the storage container is preferably within the above-mentioned range. Such a container may be formed of a single layer or multilayer made of a single material, or may be formed of multilayer formed by combination of different materials.

The iminocarboxylic acid salt-containing solid composition and the production method of such a solid composition of the present invention have the above-mentioned configuration. The present invention is: a chelate compound having advantages for transportation and storage, having excellent solubility, exhibiting functions such as excellent detergency, and useful in various applications; an iminocarboxylic acid salt-containing solid composition useful in various cleanings in various field or useful in cleanings with automatic dish washers for household or business use; and a production method of such a solid composition.

BEST MODE FOR CARRYING OUT THE INVENTION

The present invention will, hereinafter, be described in more detail with reference to Examples, but the present invention is not limited to only these Examples. The terms, "part" and "%" represent "part by weight" and "% by weight", respectively, unless otherwise specified.

As the moisture content in the HIDS acid salt, the HIDS acid salt was measured for loss on drying after heated to 200° C. at 10° C./minute and then maintained at 200° C. for 30 minutes with a differential thermal analyzer.

SYNTHESIS EXAMPLE 1

Epoxysuccinic acid disodium salt 1761 g, L-aspartic acid disodium salt 1770 g, and water 3100 g were mixed, and reacted at 90° C. for 4 hours to prepare a 50% by weight aqueous solution of 3-hydroxy iminodisuccinic acid tetrasodium salt (HIDS4Na). The 50% by weight aqueous solution of HIDS4Na was dried with a spray dryer (product of fujisaki electric Co., Ltd.) to obtain powders containing L-HIDS4Na having the aspartic acid skeleton represented by the above formula (2) of L-form. During the drying process, no sticking substances adhered to the wall surface, the pipe, and the like of the equipment.

The obtained powders were analyzed for content of the L-HIDS4Na with a high speed liquid chromatography, which shows that the content of the L-HIDS4Na was 81% by weight. The obtained powders were also analyzed for moisture content with a differential thermal analyzer, which shows that the moisture content was 10% by weight.

SYNTHESIS EXAMPLE 2

Powders containing D-HIDS4Na having the aspartic acid skeleton represented by the above formula (2) of D-form were obtained by performing reaction and drying in the same manner as in Synthesis Example 1, except that the L-aspartic acid disodium salt was replaced with D-aspartic acid disodium salt.

The obtained powders were analyzed for content of the D-HIDS4Na with a high speed liquid chromatography, which shows that the content of the D-HIDS4Na was 80% by weight. The obtained powders were also analyzed for moisture content with a differential thermal analyzer, which shows that the moisture content was 10% by weight.

EXAMPLES 1 TO 3 AND COMPARATIVE EXAMPLE 1

The L-HIDS4Na synthesized in Synthesis Example 1 was dried with a tray dryer, or the moisture of the L-HIDS4Na was absorbed within a thermo-hygrostat in which the temperature was 25° C. and the humidity was 80%. Thereby, the powder composition was adjusted such that the L-HIDS4Na had a moisture content shown in Table 1. The powder composition 0.5 g was added into water 10 g at 5° C. and measured for dissolution rate. The dissolution rate was measured through visual comparison with a reference solution. An aqueous solution in which L-HIDS4Na was previously dissolved was used as the reference solution. The time taken for the dissolution was measured as follows: time when the powder compositions were charged was defined as start, and time when the solid content was solved under stirring and evaluated to be equal to the reference solution through visual observation was defined as completion.

Dissolution rate=(charged powder composition (mg))/(time taken for dissolution (sec))

TABLE 1

|  | Moisture content (% by weight) | Content of L-HIDS4Na (% by weight) | Dissolution rate (mg/sec) |
| --- | --- | --- | --- |
| Example 1 | 4 | 86 | 8.3 |
| Example 2 | 10 | 81 | 3.0 |
| Example 3 | 16 | 76 | 2.6 |
| Comparative Example 1 | 22 | 68 | 1.6 |

EXAMPLES 4 TO 6

Powder compositions A to C were obtained by varying the mixed ratio of the L-HIDS4Na to the D-HIDS4Na each synthesized in Synthesis Examples 1 and 2 as shown in Table 2. Powder compositions A to C that could pass through 100 mesh were used for the measurement of the dissolution rate.

Each of the powder compositions A to C was added into water 10 g at 5° C. and then measured for dissolution rate. The dissolution rate was measured by the same manner as in Example 1.

Dissolution rate=(charged powder composition (mg))/(time taken for dissolution (sec))

TABLE 2

|  | Ratio of D-HIDS4Na | Ratio of L-HIDS4Na |
| --- | --- | --- |
| Powder A | 0 | 1 |
| Powder B | 1 | 0 |
| Powder C | 0.5 | 0.5 |

TABLE 3

|  | Sample | Dissolution rate (mg/sec) |
| --- | --- | --- |
| Example 4 | Powder A | 2.9 |
| Example 5 | Powder B | 3.0 |
| Example 6 | Powder C | 0.6 |

COMPARATIVE EXAMPLE 2

The moisture in the powder composition C was absorbed within a thermo-hygrostat and thereby the powder composition was adjusted to have a moisture content as shown in Table 4. Then, the powder composition 0.5 g was added into water 10 g at 5° C. and then measured for dissolution rate. The dissolution rate was measured by the same method as in Example 1.

TABLE 4

|  | Moisture content (% by weight) | Content of L-HIDS4Na (% by weight) | Dissolution rate (mg/sec) |
| --- | --- | --- | --- |
| Comparative Example 2 | 24 | 68 | 0.5 |

EXAMPLES 7 TO 11 AND REFERENCE EXAMPLES 1 AND 2

The powder composition A about 3 g was charged into an aluminum cup, and stored for one week in a thermo-hygrostat of a temperature of 25° C. and a relative humidity shown in Table 5. Then, the powder composition A was measured for change in weight, and an increase ratio of weight was calculated according to the following formula.

$$\text{Increase ratio of weight}(\%) = \frac{(\text{weight of powder } A \text{ after one week(g)}) - (\text{weight of powder } A \text{ when charged(g)})}{(\text{weight of powder } A \text{ when charged(g)})} \times 100$$

TABLE 5

|  | Relative humidity (%) | Increase ratio of weight (%) |
| --- | --- | --- |
| Example 7 | 10 | 0 |
| Example 8 | 30 | 0 |
| Example 9 | 35 | 0 |
| Example 10 | 38 | 0 |
| Example 11 | 40 | 0 |
| Reference Example 3 | 43 | 7.8 |
| Reference Example 4 | 45 | 10.3 |

EXAMPLES 12 TO 14

The powder compound A 500 g was charged into a bag (storage container) made of a material shown in Table 6, and the bag was sealed by performing heal seat. This bag was stored in a thermo-hygrostat of a temperature of 25° C. and a relative humidity of 60% for one month, and the powder composition was observed for the state.

TABLE 6

|  | Material of storage container | Thickness of storage container (μm) | State of powder |
| --- | --- | --- | --- |
| Example 12 | Aluminum | 6.5 | Dried powder |
| Example 13 | Polyethylene | 80 | Dried powder |

The present application claims priority to Japanese Patent Application No. 2005-217887 filed in Japan on Jul. 27, 2005, the entire contents of which are herein incorporated by reference.

The invention claimed is:

1. A solid composition comprising an iminocarboxylic acid compound,
wherein the iminocarboxylic acid compound is 3-hydroxy-2,2'-iminodisuccinic acid and/or a salt thereof,
the solid composition comprises 70% by weight or more and 90.5% by weight or less of the iminocarboxylic acid compound, relative to a solid content except for moisture of the solid composition, and the solid composition comprises 20% by weight or less of moisture, relative to the solid composition, and wherein an isomer ratio (a D-form/L-form molar ratio) of an aspartic acid skeleton of the iminocarboxylic acid compound is 0/1 to 0.3/0.7 or 1/0 to 0.7/0.3, and wherein the solid composition has a particle size of 0.1 μm to 100 μm and wherein the solid composition is obtainable by a method comprising a drying step using spray drying equipment, and wherein said composition has 0.6 mg/sec or more of a dissolution ratio calculated from the following formula, at 5° C.:
Dissolution rate=(charged powder composition (mg))/ time taken for dissolution (sec)).

2. A production method of the solid composition of claim 1, comprising a step of drying an iminocarboxylic acid compound-containing composition.

3. A storage method of the solid composition of claim 1, wherein the solid composition is stored under an atmosphere of 42% or less relative humidity at 25° C.

4. The solid composition according to claim 1, which comprises 18% by weight or less of moisture, relative to the solid composition.

5. The solid composition according to claim 4, which comprises 15% by weight or less of moisture, relative to the solid composition.

6. The solid composition according to claim 1, which comprises 75% by weight or more and 90.5% by weight or less of the iminocarboxylic acid compound relative to a solid content except for moisture of the solid composition.

7. The solid composition according to claim 6, which comprises 80% by weight or more and 90.5% by weight or less of the iminocarboxylic acid compound relative to a solid content except for moisture of the solid composition.

8. The solid composition according to claim 1, wherein the dissolution ratio at 5° C. is 1.8 mg/sec or more.

9. The solid composition according to claim 1, wherein the dissolution ratio at 5° C. is 2.0 mg/sec or more.

10. A storage method of the solid composition according to claim 3,
wherein the solid composition is stored in a storage container, and the thickness of the storage container is 0.005 mm to 0.5 mm.

* * * * *

UNITED STATES PATENT AND TRADEMARK OFFICE
CERTIFICATE OF CORRECTION

PATENT NO.        : 8,173,588 B2
APPLICATION NO.   : 11/492900
DATED             : May 8, 2012
INVENTOR(S)       : Tomomi Ina et al.

It is certified that error appears in the above-identified patent and that said Letters Patent is hereby corrected as shown below:

In the Claims:

At column 11, claim number 1, line number 23, "at 5° C.:" should read --at 5° C:--

At column 12, claim number 8, line number 19, "5° C. is" should read --5° C is--

At column 12, claim number 9, line number 21, "5° C. is" should read --5° C is--

Signed and Sealed this
Fourteenth Day of August, 2012

David J. Kappos
*Director of the United States Patent and Trademark Office*